United States Patent [19]
Hori et al.

[11] Patent Number: 5,916,771
[45] Date of Patent: Jun. 29, 1999

[54] PRODUCTION OF A MULTIMERIC PROTEIN BY CELL FUSION METHOD

[75] Inventors: Nobuaki Hori, Kawasaki, Japan; Claude Geoffrey Davis, Burlingame, Calif.; Krisztina M. Zsebo, Woodside, Colo.; Aya Jakobovits, Menlo Park, Calif.

[73] Assignees: Abgenix, Inc., Fremont, Calif.; Japan Tobacco Inc., Tokyo, Japan

[21] Appl. No.: 08/730,639

[22] Filed: Oct. 11, 1996

[51] Int. Cl.$^6$ ............................ C12P 21/04; C12N 15/00; C12N 5/06; C12N 5/12

[52] U.S. Cl. .................... 435/69.6; 536/23.1; 536/23.5; 536/23.53; 435/320.1; 435/326; 435/70.21; 435/346; 530/395; 530/387.1

[58] Field of Search .................... 536/23.5, 23.1, 536/23.53; 530/395, 387.1; 435/326, 320.1, 70.21, 346, 69.6

[56] References Cited

U.S. PATENT DOCUMENTS

| | | |
|---|---|---|
| 4,816,397 | 3/1989 | Boss et al. . |
| 4,816,567 | 3/1989 | Cabilly et al. . |
| 4,975,369 | 12/1990 | Beavers et al. . |
| 5,202,238 | 4/1993 | Fell et al. . |
| 5,643,745 | 7/1997 | Stuart . |
| 5,683,899 | 11/1997 | Stuart . |
| 5,695,965 | 12/1997 | Stuart et al. . |

FOREIGN PATENT DOCUMENTS

| | | |
|---|---|---|
| 0 273 889 | 7/1988 | European Pat. Off. . |
| 0 088 994 B1 | 6/1991 | European Pat. Off. . |
| WO 86/01533 | 3/1986 | WIPO . |
| WO 92/15322 | 9/1992 | WIPO . |
| WO 93/19172 | 9/1993 | WIPO . |
| WO 93/25663 | 12/1993 | WIPO . |
| WO 94/02602 | 2/1994 | WIPO . |
| WO 95/02686 | 1/1995 | WIPO . |
| WO 95/30739 | 11/1995 | WIPO . |

OTHER PUBLICATIONS

Wood, et al., "High Level Synthesis of Immunoglobulins in Chinese Hamster Ovary Cells," *J. Immunol.* 145(9):3011–3016 (Nov. 1, 1990).

Bebbington, C.R., (1991) "Expression of Antibody Genes in Nonlymphoid Mammalian Cells," *Methods: A Companion to Methods Enzymol.* 2:136–145.

Bebbington, C.R., et al., (1992) "High–level Expression of a Recombinant Antibody from Myeloma Cells Using a Glutamine Synthetase Gene As An Amplifiable Selectable Marker," *Bio/Technology* 10:169–175.

Caron, P.C., et al., (1992) "Engineered Humanized Dimeric Forms of IgG Are More Effective Antibodies," *J. Exp. Med.* 176:1191–1195.

Cattaneo, A. and Neuberger, M.S., (1987) "Polymeric Immunoglobulin M Is Secreted by Transfectants of Non–lymphoid Cells in the Absence of Immunoglobulin J Chain," *EMBO J.* 6:2753–2758.

Cockett, M.I., et al., (1990) "High–level Expression of Tissue Inhibitor of Metalloproteinases in Chinese Hamster Ovary Cells Using Glutamine Synthetase Game Amplification," *Bio/Technology* 8:662–667.

Graham, F.L., and Vander Eb, A.J., (1973) "A New Technique for the Assay of Infectivity of Human Adenovirus 5 DNA," *Virology* 52:456–467.

Riechmann, L. et al., (1988) "Reshaping Human Antibodies for Therapy," *Nature* 332:323–327.

Kranenborg, et al., "Development and Characterization of Anti–Renal Cell Carcinoma X Antichelate Bispecific Monoclonal Antibodies for Two–Phase Targeting of Renal Cell Carcinoma," *Cancer Research* (Dec. 1995), vol. 55, No. 23, pp. 5864S–5867S.

Cao, et al., "A Rapid Non–Selective Method to Generate Quadromas by Microelectrofusion," *J. Immunol. Methods* (Nov. 16, 1995), vol. 187, No. 1, pp. 1–7.

Salazar–Kish, et al., "Comparison of a Quadroma and its Parent Hybridomas in Fed Batch Culture," *J. Biotechnology* (1993), vol. 30, No. 3, pp. 351–365.

Bos, et al., "Enhanced Transfusion of a Bacterial Plasmid of Hybrid Hybridoma (Quadroma Cell) Lines," *Hybridoma* (Feb. 1992), vol. 11, No. 1, pp. 41–51.

*Primary Examiner*—Paula K. Hutzell
*Assistant Examiner*—Geetha P. Bansal
*Attorney, Agent, or Firm*—Carol L. Francis; Bozicevic, Field & Francis LLP

[57] ABSTRACT

The present invention features a method of producing a multimeric protein from a hybrid cell formed from the fusion of two or more cells, each of which cell is engineered to express one component of the multimeric protein, as well as a method for screening for successful fusion of the cells to produce a desired hybrid cell. The methods of the invention are widely applicable to the production of proteins having two or more components.

11 Claims, 4 Drawing Sheets

FIG. 1

FIG. 2 Hybrid cell containing and expressing both heavy and light chain DNAs

PRODUCTION OF A MULTIMERIC PROTEIN BY CELL FUSION METHOD

FIELD OF THE INVENTION

This invention relates generally to methods for use in gene expression and cell fusion techniques, particularly in the production of multi-component proteins.

BACKGROUND OF THE INVENTION

Recombinant DNA techniques have been used for production of heterologous proteins in transformed host cells. Generally, the produced proteins are composed of a single amino acid chain or two chains cleaved from a single polypeptide chain. More recently, multichain proteins such as antibodies have been produced by transforming a single host cell with DNA sequences encoding each of the polypeptide chains and expressing the polypeptide chains in the transformed host cell (U.S. Pat. No. 4,816,397).

The basic immunoglobulin (Ig) structural unit in vertebrate systems is composed of two identical "light" polypeptide chains (approximately 23 kDa), and two identical "heavy" chains (approximately 53 to 70 kDa). The four chains are joined by disulfide bonds in a "Y" configuration, and the "tail" portions of the two heavy chains are bound by covalent disulfide linkages when the immunoglobulins are generated either by hybridomas or by B cells.

Figure 1:
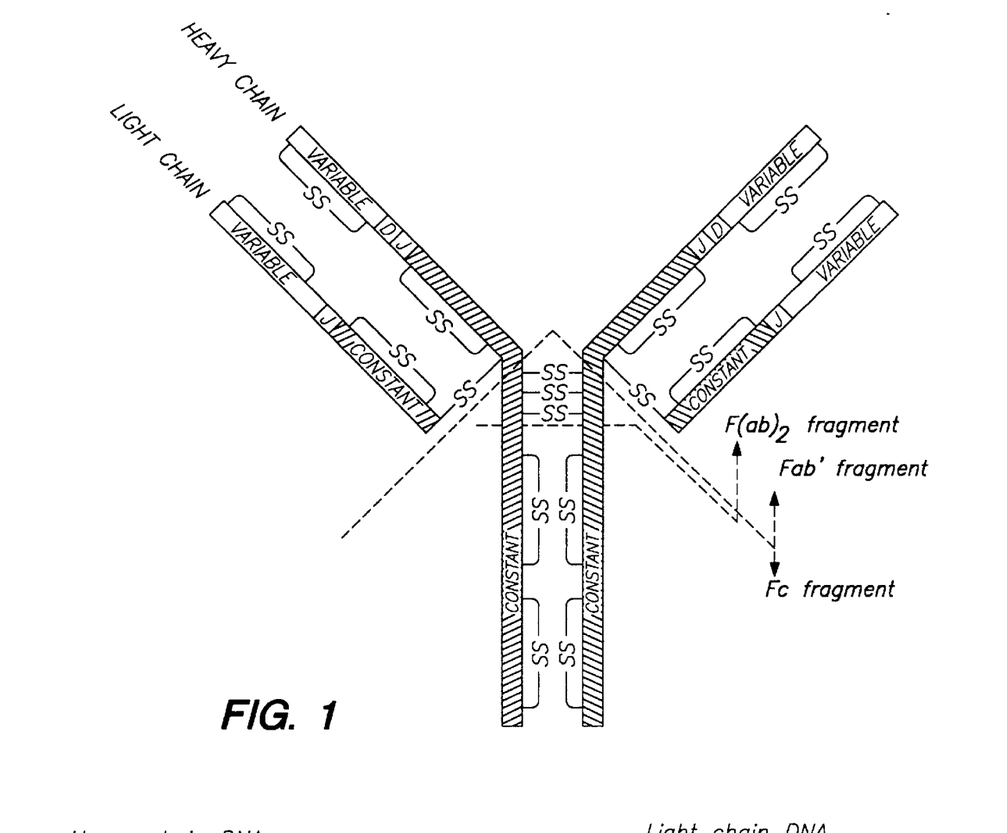
FIG. 1 is a schematic showing the basic immunoglobulin structure.

A schematic of the general antibody structure is shown in FIG. 1. The light and heavy chains are each composed of a variable region at the N-terminal end, and a constant region at the C-terminal end. In the light chain, the variable region (termed "$V_L J_L$") is the product of the recombination of a $V_L$ gene to a $J_L$ gene. In the heavy chain, the variable region ($V_H D_H J_H$) is the product of recombination of first a $D_H$ and a $J_H$ gene, followed by a $D_H J_H$ to $V_H$ recombination. The $V_L J_L$ and $V_H D_H J_H$ regions of the light and heavy chains, respectively, are associated at the tips of the Y to form the antibody's antigen binding domain and together determine antigen binding specificity.

The ($C_H$) region defines the antibody's isotype, i.e., its class or subclass. Antibodies of different isotypes differ significantly in their effector functions, such as the ability to activate complement, bind to specific receptors (Fc receptors) present on a wide variety of cell types, cross mucosal and placental barriers, and form polymers of the basic four-chain IgG molecule.

Antibodies are categorized into "classes" according to the $C_H$ type utilized in the immunoglobulin molecule (IgM, IgG, IgD, IgE, or IgA). There are at least five types of $C_H$ genes ($C\mu$, $C\gamma$, $C\delta$, $C\epsilon$, and $C\alpha$), and some species (including humans) have multiple $C_H$ subtypes (e.g., $C\gamma_1$, $C\gamma_2$, $C\gamma_3$, and $C\gamma_4$ in humans). There are a total of nine $C_H$ genes in the haploid genome of humans, eight in mouse and rat, and several fewer in many other species. In contrast, there are normally only two types of light chain constant regions ($C_L$), kappa (κ) and lambda (λ), and only one of these constant regions is present in a single light chain protein (i.e., there is only one possible light chain constant region for every $V_L J_L$ produced). Each heavy chain class can be associated with either of the light chain classes (e.g., a $C_H\gamma$ region can be present in the same antibody as either a κ or λ light chain).

A process for the immortalization of B cell clones producing antibodies of a single specificity has been developed involving fusing B cells from the spleen of an immunized mouse with immortal myeloma cells. Single clones of fused cells secreting the desired antibody could then be isolated by drug selection followed by immunoassay. These cells were given the name "hybridoma" and their antibody products termed "monoclonal antibodies."

The use of monoclonal antibodies as therapeutic agents for human disease requires the ability to produce large quantities of the desired antibody. One approach to increased production was simply to scale up the culture of hybridoma cells. Although this approach is useful, it is limited to production of that antibody originally isolated from the mouse. In the case where a hybridoma cell produces a high affinity monoclonal antibody with the desired biological activity, but has a low production rate, the gene encoding the antibody can be isolated and transferred to a different cell with a high production rate.

In some cases it is desirable to retain the specificity of the original monoclonal antibody while altering some of its other properties. For example, a problem with using murine antibodies directly for human therapy is that antibodies produced in murine systems may be recognized as "foreign" proteins by the human immune system, eliciting a response against the antibodies. A human anti-murine antibody (HAMA) response results in antibody neutralization and clearance and/or potentially serious side-effects associated with the anti-antibody immune response. Such murine-derived antibodies thus have limited therapeutic value.

One approach to reducing the immunogenicity of murine antibodies is to replace the constant domains of the heavy and light chains with the corresponding human constant domains, thus generating human-murine chimeric antibodies. Chimeric antibodies are generally produced by cloning the antibody variable regions and/or constant regions, combining the cloned sequences into a single construct encoding all or a portion of a functional chimeric antibody having the desired variable and constant regions, introducing the construct into a cell capable of expressing antibodies, and selecting cells that stably express the chimeric antibody. Examples of methods using recombinant DNA techniques to produce chimeric antibodies are described in PCT Publication No. WO 86/01533 (Neuberger et al.), and in U.S. Pat. Nos. 4,816,567 (Cabilly et al.) and 5,202,238 (Fell et al.).

In another approach, complementarity determining region (CDR)-grafted humanized antibodies have been constructed by transplanting the antigen binding site, rather than the entire variable domain, from a rodent antibody into a human antibody. Transplantation of the hypervariable regions of an antigen-specific mouse antibody into a human heavy chain gene has been shown to result in an antibody retaining antigen-specificity with greatly reduced immunogenicity in humans (Riechmann et al. (1988) Nature 332:323–327; Caron et al. (1992) J. Exp. Med 176:1191–1195).

Another approach in the production of human antibodies has been the generation of human B cell hybridomas. Applications of human B cell hybridoma-produced monoclonal antibodies have promising potential in the treatment of cancer, microbial infections, B cell immunodeficiencies associated with abnormally low antibody production, and other diseases and disorders of the immune system. Obstacles remain in the development of such human monoclonal antibodies. For example, many human tumor antigens may not be immunogenic in humans and thus it may be difficult to isolate anti-tumor antigen antibody-producing human B cells for hybridoma fusion.

For a given disease indication, one antibody isotype is likely to be greatly preferred over another. The preferred isotype may vary from one indication to the next. For example, to treat cancer it may be desirable that the binding of an antibody to a tumor cell result in killing of a tumor cell. In this case, an IgG1 antibody, which mediates both antibody-dependent cellular cytotoxicity and complement fixation, would be the antibody of choice. Alternatively, for treating an autoimmune disease, it may be important that the antibody only block binding of a ligand to a receptor and not cause cell killing. In this case, an IgG4 or IgG2 antibody would be preferred. Thus, even in a situation where a high affinity, antigen-specific, fully human antibody has been isolated, it may be desirable to re-engineer that antibody and express the new product in a different cell.

The growing use of phage display technology also points to a need for antibody engineering and expression methodologies. Phage display technology is used for producing libraries of antibody variable domains cloned into bacteria. This allows variable domains of desired specificity to be selected and manipulated in vitro. While bacteria offer a great advantage for selecting and producing antibody fragments, they are not capable of producing full-size intact antibodies in native configuration, and it is necessary to reconstitute fragments selected in bacteria into intact antibodies and express them in eucaryotic cells.

SUMMARY OF THE INVENTION

The present invention features a method of producing a multimeric protein from a hybrid cell formed from the fusion of two or more cells, each of which cell is engineered to express one component of the multimeric protein, as well as a method for screening for successful fusion of the cells to produce a desired hybrid cell. The methods of the invention are widely applicable to the production of proteins having two or more components.

In one specific application of the method of the invention, the multimeric protein is an antibody composed of antigen-specific heavy and light chains. DNA encoding the desired heavy chain (or a fragment of the heavy chain) is introduced into a first mammalian host cell, while DNA encoding the desired light chain (or a fragment of the light chain) is introduced into a second mammalian host cell. The first transformed host cell and the second transformed host cell are then combined by cell fusion to form a third cell. Prior to fusion of the first and second cells, the transformed cells may be selected for specifically desired characteristics, e.g., high levels of expression. After fusion, the resulting hybrid cell contains and expresses both the DNA encoding the desired heavy chain and the DNA encoding the desired light chain, resulting in production of the multimeric antibody.

In one aspect the invention features the multimeric protein produced by the method of the invention. In one embodiment, the invention includes an antibody produced by the method of the invention.

In another aspect the invention features a method for screening for successful fusion of a first cell containing a first nucleotide sequence encoding a desired antibody heavy chain and a second cell containing a second nucleotide sequence encoding a desired antibody light chain, the method comprising including a nucleotide sequence encoding a first marker gene in the first cell, including a nucleotide sequence encoding a second marker gene in the second cell, fusing the first and second cells to produce a fused cell and assaying for the presence of the first and second marker genes in the fused cell.

One advantage of the method of the invention is that cells expressing a single component of the final multi-component protein can be individually selected for one or more desired characteristics, such as a high rate of production.

Another advantage is that the method generates a cell which produces an antibody at a multiplication high rate through the fusion of two kinds of cells which are each selected prior to fusion for high production of the desired heavy or light chains.

Another advantage is that the final multi-component protein is not expressed until all the cells expressing the individual components of the multi-component protein are fused into a single hybrid cell.

Other aspects, features, and advantages of the invention will become apparent from the following detailed description, and the claims.

DETAILED DESCRIPTION

Before the methods and compositions of the present invention are described and disclosed it is to be understood that this invention is not limited to the particular methods and compositions described as such may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "an" and "the" include plural references unless the context clearly dictates otherwise. Thus, for example, reference to "a DNA sequence" includes a plurality of DNA sequences and different types of DNA sequences.

Unless defined otherwise all technical and scientific terms used herein have the same meaning as commonly understood by one of ordinary skill in the art to which this invention belongs. Although any materials or methods similar or equivalent to those described herein can be used in the practice or testing of the present invention, the preferred methods and materials are now described. All publications mentioned herein are incorporated herein by reference for the purpose of describing and disclosing the particular information for which the publication was cited. The publications discussed above are provided solely for their disclosure prior to the filing date of the present application. Nothing herein is to be construed as an admission that the inventor is not entitled to antedate such disclosure by virtue of prior invention.

Definitions

By the term "nucleotide sequence" is meant any DNA fragment of interest which may be introduced into a cell, including an intact gene or fragment of a gene. When the method of the invention is used to generate an antibody, the nucleotide sequence of interest will be all or part of either the constant region and/or variable region of the light or heavy chains, and may include all, part, or none of the regulatory nucleotide sequences that control expression of the light or heavy chain. The nucleotide sequence of interest for heavy chains includes but is not limited to all or a portion of the V, D, J, and switch regions (including intervening sequences) and flanking sequences. For light chains, the nucleotide sequence of interest includes but is not limited to the V and J regions, and flanking and intervening sequences. The nucleotide sequence may be a naturally occurring sequence, synthetic, or partially natural and partially synthetic. The sequence may also be a non-naturally occurring or modified naturally-occurring sequence. The DNA sequence includes sequences taken from different sources, e.g., different species. For example, when the method is used to produce an antibody, the DNA chain may encode a chimeric (for example, human-mouse) immunoglobulin chain, or it may be a CDR-grafted DNA sequence having a human immunoglobulin sequence with antigen-specific murine CDR sequences. The DNA of the nucleotide sequence may encode a fully human antibody. B-cells obtained from non-human animals immunized with an antigen and also hybridoma, trioma, and quadromas derived from such B-cells can also provide the nucleotide sequence introduced into the host cells. B-cells and hybridomas producing any kind of monoclonal antibody may be used as a source of the nucleotide sequence, including cells producing, for example, fully mouse monoclonal antibodies, fully human monoclonal antibodies, CDR-grafted monoclonal antibodies, chimeric monoclonal antibodies, and F(ab)$_2$.

By the terms "multi-component", "multichain", or "multimeric" protein is meant a protein composed of two or more proteins or polypeptides. The method of the invention is useful for producing a multimeric protein by the fusion of two or more cells each expressing a single component of the multimeric protein. For example, in one embodiment the multi-component protein is an antibody generated from two heavy chains encoded by DNA transfected into a first cell and two light chains encoded by DNA transfected into a second cell, where the final multimeric antibody is produced by a hybrid cell formed from the fusion of the first and second cells. "Multi-component," "multichain," and "multimeric" protein is meant to include any heterodimeric or hetero-oligomeric protein (e.g., BMP2/BMP7 heterodimeric osteogenic protein, ICE (interleukin-1 converting protein), receptors of the nucleus (e.g., retinoid receptors), heterodimeric cell surface receptors (e.g., T cell receptors), integrins (e.g, cell adhesion molecules, $\beta_1$-integrins, (see, e.g., Hynes, 1987 Cell 48:549–554; Hynes 1992 Cell 60:11–25), tumor necrosis factor (TNF) receptor, and soluble and membrane-bound forms of class I and class II MHC (major histocompatibility complex proteins). Where the multimeric protein is a receptor, "multimeric protein" is meant to encompass soluble and membrane forms of the receptor.

By the term "introducing" a nucleotide sequence into a cell means inserting an exogenous piece of DNA into a cell, including but not limited to transfection or transduction with a vector, such that all or part of the exogenous nucleotide sequence is stably maintained in the cell, and the resulting transformed cell expresses the introduced nucleotide sequence.

By the term "fusing" or "fusion" of two or more cells is meant a method in which two or more cells are combined to form a single hybrid cell which contains all or part of at least the nucleic acid content of each individual cell. Fusion may be accomplished by any method of combining cells under fuseogenic conditions well known in the art (See, for example, Harlow & Lane (1988) in *Antibodies*, Cold Spring Harbor Press, New York). Known methods for fusing cells includes by use with polyethylene glycol (PEG) or Sendai virus.

By the term "hybrid cell" is meant a cell formed by combining two or more cells, e.g., by fusion. In the method of the invention, hybrid cells are formed from the fusion of one or more transformed cells each expressing a single component of a multimeric protein.

The term "irrelevant" as in, e.g., "an irrelevant light chain" means a light chain which does not contribute to the binding of the antigen of interest and is not a component of the multimeric protein produced by the hybrid cell of the invention.

By the term "desired" component, e.g., desired heavy chain, or desired light chain, is meant an immunoglobulin chain which recognizes the antigen of interest.

Generation of a Hybrid Cell Producing a Heterologous Multimeric Protein

The present invention provides a method for generating a hybrid cell producing a multi-component protein from two or more transformed cells each of which cells produces a single component of the multimeric protein. This method features several important advantages relative to conventional methods for protein production. For example, the method of the present invention allows separately transformed cells to be individually selected for optimal expression of each component of the multi-component protein. This selection occurs prior to fusion of cells forming the hybrid cell and prior to production of the final multimeric protein. The method of the invention results in a final multi-component protein product which is not expressed until a single hybrid cell is produced from the fusion of each cell expressing a component of the final protein product.

Figure 2:
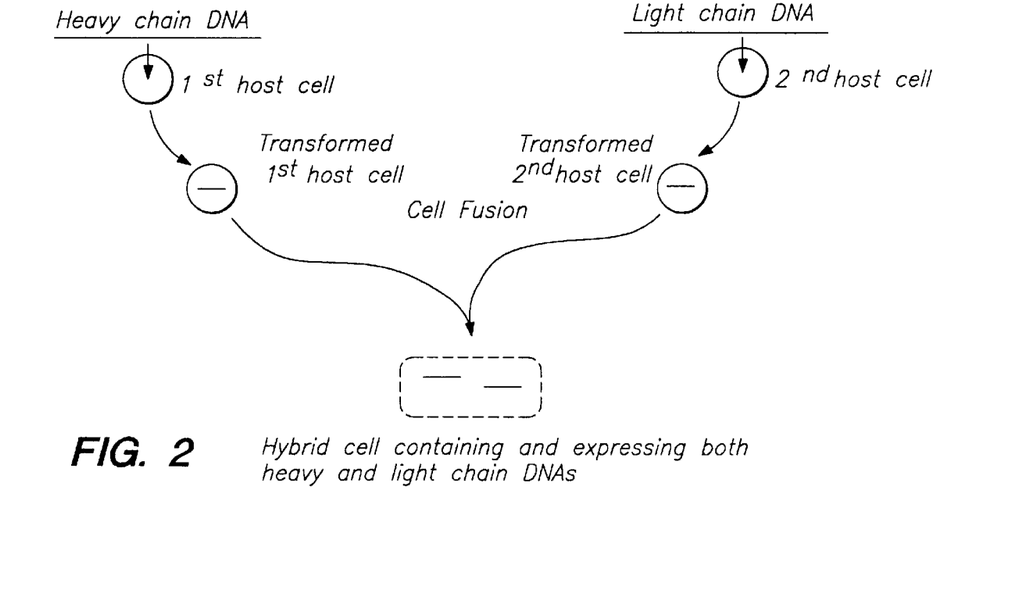
FIG. 2 is a flow chart showing one embodiment of the method of invention when mammalian cells are separately transformed with the desired light and heavy chain DNA, then fused to form the hybrid cell expressing both chains.

Generally, when the multi-component protein to be produced is an antibody, the method of the invention involves generation of a cell expressing a desired heavy chain, generation of a cell expressing a desired light chain, and fusion of the two cells to form a hybrid cell expressing the final antibody protein (FIG. 2). Generation of a cell expressing the desired heavy chain involves the following steps: (1) identifying and cloning and/or synthesizing the gene, gene fragment, or nucleotide sequence encoding the variable segment or antigen-binding sequences of the heavy chain. The nucleotide sequence may be obtained from either a cDNA or genomic source, or synthesized de novo; (2) cloning the nucleotide sequence encoding the desired constant regions of the heavy chain; (3) ligating the variable region with the constant region so that the complete nucleotide sequence can be transcribed and translated to express the desired heavy chain polypeptide; (4) ligating the construct into a vector containing a selectable marker and appropriate gene control regions; (5) amplifying the construct in bacteria; (6) introducing the vector into eukaryotic cells; (7) selecting the cells expressing the selectable marker; and (8) screening the cell supernatants or lysates for the expressed heavy chain. Similarly, a cell expressing a desired light chain construct is generated as outlined above.

Alternatively, the process of generating a cell expressing a desired heavy or light chain may involve (1) construction of a Ig chain DNA sequence containing (a) a signal sequence, (b) the gene, gene fragment, or nucleotide sequence encoding the variable region or antigen-binding sequences, and (c) the nucleotide sequence encoding the desired constant region of the Ig chain, followed by (2) PCR amplification of the Ig construction, (3) insertion of the construct into eukaryotic cells, (4) selecting the cells expressing the selectable marker, and (5) screening the cells for the expressed Ig chain. Optionally, the cells expressing the desired heavy chain or the desired light chain can be further selected for desirable characteristics, such as heavy or light chain production rate or level, ability of the expressed heavy or light chain to combine with another light or heavy chain, respectively, to provide an antibody having a desired antigen binding affinity, and/or other characteristics desirable for heavy or light chain production or function in an antibody.

Transformed cells expressing or capable of expressing the desired component of the multimeric protein are fused by methods known in the art to form a hybrid cell expressing the multimeric protein. When the multimeric protein is an antibody, the DNA sequences encoding the desired immunoglobulin may be composed entirely of sequences originating from a single species, e.g., fully human or fully murine, or may be contain sequences originating from more than one species, e.g., a human-mouse chimera or CDRgrafted humanized antibody. The hybrid cell produced antibody product may also contain a desired antigen binding site (variable region) linked to a desired constant region. Thus, a specifically designed antibody may be generated with a desired antigenicity combined with the desired isotype.

Prior art methods for independently expressing the light and heavy chains in a single host cells are known, see, for example, U.S. Pat. No. 4,816,397, European patent application publication No. 88,994, PCT published patent application WO 93/19172, U.S. Pat. No. 4,816,567, U.S. Pat. No. 4,975,369, U.S. Pat. No. 5,202,238, PCT published patent application WO 86/01533, PCT published patent application WO 94/02602, and European published patent application No. 273,889.

Vector Constructs

The vectors of the invention are recombinant DNA vectors including, but not limited to, plasmids, phages, phagemids, cosmids, viruses, retroviruses, and the like, which insert a nucleotide sequence into a cell.

Methods for introducing an exogenous nucleotide sequence of interest into a cell, including into antibody-producing cells, are known in the art. These methods typically include use of a DNA vector to introduce the nucleotide sequence into the genome or a cell or cells, and then growing the cells to generate a suitable population. Nucleotide sequences may also be introduced directly into a cell by methods known in the art.

In a preferred embodiment, nucleotide sequences are introduced into mammalian cells according to the $CaPO_4$ transfer procedure described by Graham and van der Eb (1973) Virology 52:456–467, herein specifically incorporated by reference. Transfection of mammalian cell lines may be accomplished by any of a number of methods known to those skilled in the art, including but not limited to, $CaPO_4$ precipitation, electroporation, microinjection, liposome fusion, RBC ghost fusion, protoplast fusion, and the like.

DNA Sequences

The nucleotide sequence encoding a component of the desired multi-component protein may be obtained as a cDNA or as a genomic DNA sequence by methods known in the art. For example, messenger RNA coding for a desired component may be isolated from a suitable source employing standard techniques of RNA isolation, and the use of oligo-dT cellulose chromatography to segregate the poly-A mRNA. When the product multi-component protein is an antibody, suitable sources of desired nucleotide sequences may be isolated from mature B cells or a hybridoma culture.

In addition to the nucleotide sequence encoding the desired component of the product multi-component protein, vector constructs can include additional components to facilitate replication in prokaryotic and/or eukaryotic cells, integration of the construct into a eukaryotic chromosome, and markers to aid in selection of and/or screening for cells containing the construct (e.g., the detectable markers and drug resistance genes discussed above for the targeting construct). For eukaryotic expression, the construct should preferably additionally contain a polyadenylation sequence positioned 3' of the gene to be expressed. The polyadenylation signal sequence may be selected from any of a variety of polyadenylation signal sequences known in the art. Preferably, the polyadenylation signal sequence is the SV40 early polyadenylation signal sequence.

Transformation of Host Cells

Antibodies have been expressed in a variety of host cells, including bacterial, yeast, and insect cells. For the production of large, multimeric proteins, mammalian cell expression systems generally provide the highest level of secreted product (Bebbington (1991) Methods: A Companion to Methods Enzymol. 2:136–145). Myeloma cells have been used as fusion partners for splenic cells to generate hybridomas cells expressing antibodies. Transformed myeloma cells may be used as fusable host cells in the method of the invention.

Host Cells

Nonlymphoid cells lines have been investigated for use in producing antibodies (Cattaneo & Neuberger (1987) EMBO J. 6:2753–2758; Deans et al. (1984) Proc. Natl. Acad. Sci. 81:1292–1296; Weidle et al. (1987) Gene 51:21–29). The ability of nonlymphoid cell lines to assemble and secrete fully functional antibodies may be exploited for antibody production. For example, Chinese hamster ovary (CHO) cells and COS cells have well-characterized efficient expression systems and have been used for both long-term and transient expression of a variety of proteins (Bebbington (1991) supra). A method for achieving a high level of expression of DNA sequences encoding a chimeric antibody in transformed NSO myeloma cells has been described (Bebbington et al. (1992) Bio/Technology 10:169–175).

Any mammalian cell line capable of expressing the desired multimeric protein and amenable to fusion is suitable for use in the present invention. For example, where the desired protein is an antibody, the cell line is any mammalian cell capable of expressing a functional antibody. A preferred host cell is a mammalian myeloma cell; most preferably, an non-secreting (NS) myeloma cell (e.g., a non-secreting (NSO) myeloma). Other myeloma cells include mouse derived P3/X63-Ag8.653, P3/NS1/1-Ag4-1 (NS-1), P3/X63Ag8.U1 (P3U1), SP2/O-Ag14 (Sp2/O, Sp2), PAI, F0, and BW5147; rat derived 210RCY3-Ag.2.3; and human derived U-266AR1, GM1500-6TG-A1-2, UC729, CEM-AGR, DIR11, and CEM-T15.

Selection of Transformed Cells

Detection of transfectants with properly integrated vector sequences can be accomplished in a number of ways, depending on the nature of the integrated sequences. If the transferred nucleotide sequence includes a selectable marker, the initial screening of the transfected cells is to select those which express the marker. Any of a variety of selectable markers known in the art may be included in the construct, including dihydrofolate reductase (DHFR), guanosine phosphoryl transferase gene (gpt), neomycin resistance gene (Neo), hygromycin resistance gene (Hyg) and hypoxanthine phosphoribosyl transferase (HPRT). For example, when using a drug resistance gene, those transfectants that grow in the selection media containing the drug (which is lethal to cells that do not contain the drug resistance gene) can be identified in the initial screening. It will be appreciated that a variety of other positive, as well as negative (i.e., HSV-TK, cytosine deaminase, and the like), selectable markers that are well known in the art can be utilized in accordance with the present invention for selection of specific cells and transfection or other events. As well, a variety of other marker genes (i.e, the LacZ reporter gene and the like) can be utilized in similar manners.

After a period of time sufficient to allow selection to occur (in most cases, about 2 weeks) the surviving cells are then subjected to a second screening to identify those transfectants which express the desired peptide component of interest. This may be accomplished by, for instance, an immunoassay using antibodies specific for the particular immunoglobulin class.

The protocol for the second screening depends upon the nature of the inserted sequences. For example, where the cell is transformed with a sequence which does not result in a secreted product, selection for the presence of the foreign DNA can be detected by Southern blot using a portion of the exogenous sequence as a probe, or by polymerase chain reaction (PCR) using sequences derived from the exogenous sequence as amplifiers. The cells having an appropriately integrated sequence can also be identified by detecting expression of a functional product, e.g., immuno-detection of the product. Alternatively, the expression product can be detected using a bioassay to test for a particular effector function conferred by the exogenous sequence.

Where the first host cell is transfected with DNA encoding heavy chain, the expression of the heavy chain can be tested using any conventional immunological screening method known in the art, for example, ELISA conducted with cell lysate samples (see, for example, Colcher et al. Protein Engineering 1987 1:499–505). The cell can be further selected for additional desirable characteristics such as heavy chain production rate or level, ability of the expressed heavy chain to combine with light chain to provide an antibody of a desired antigen binding affinity, and other characteristics desirable for heavy chain production and heavy chain function in an antibody.

Nonlymphoid cells expressing a desired protein may be transfected in a number of ways known to the art. One example of the method of the invention is described in Example 1 below. A first CHO cell may be transfected with a vector comprising a DNA sequence encoding a desired light chain and a second CHO cell transfected with a vector comprising a DNA sequence encoding a desired heavy chain. Transfected cells are selected and fused. Fused cells are selected for expression of an antibody having the desired light chain Ig and heavy chain Ig.

In one embodiment, a cell expressing an Ig heavy chain gene also expresses an irrelevant Ig light chain gene. In some instances, co-expression of a light chain may be required for secretion and expression of the Ig heavy chain. Failure of a cell to secrete the heavy chain peptide may make detection of transfectants more difficult since it necessitates assaying the cells themselves (e.g., by Northern blot analysis or immuno-detection), as opposed to conveniently screening the cell supernatant by ELISA.

Figure 3:
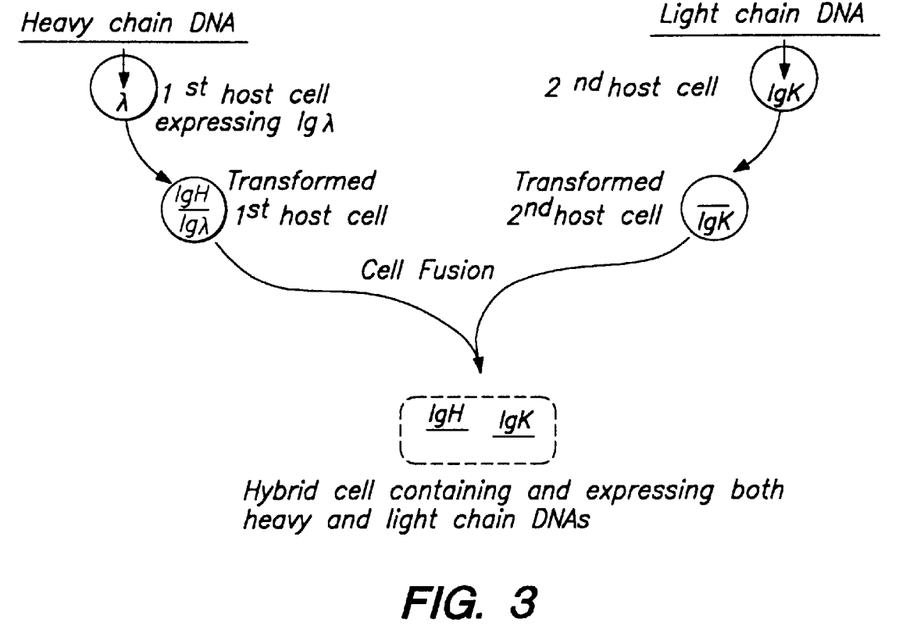
FIG. 3 illustrates a specific embodiment of the invention in which a mammalian cell expressing an irrelevant light chain is transformed with the desired heavy chain DNA, a second mammalian cell is transformed with the desired light chain DNA, and the desired hybrid cell formed from fusion of the transformed host cells is selected which expresses the desired antibody product.

In a specific embodiment of the invention, this problem is avoided by transfecting a first host cell expressing an irrelevant light chain with a plasmid bearing the desired heavy chain (FIG. 3). The gene encoding the irrelevant light chain may either be integrated into a chromosome or be present in an episomal vector, such as bovine papilloma virus (BPV) or other episomal vector known in the art. After selection for transformants, expression of the heavy chain is easily confirmed by an ELISA assay of the cell lysates for secreted antibody.

Cells expressing the desired heavy chain are then fused with a second cell that has been transfected with the desired light chain under appropriate fuseogenic conditions according to methods well known in the art (see, e.g., Harlow & Lane, supra). Any combination of cells capable of expressing a desired heavy chain or desired light chain and that can be fused to produce a hybrid cell expressing both heavy and light chains can be used. Thus, the first cell (e.g., expressing the desired heavy chain) can be of the same or different type as the second cell (e.g, expressing the desired light chain), e.g., the first cell can be a myeloma cell and the second cell can be a non-lymphoid cell. The fusion product cells which are candidates for manufacturing lines will express the desired heavy chain and light chain, but will have lost the irrelevant light chain. During the fusion process, random chromosomes are normally lost. Thus, it is expected that cells lacking the irrelevant Ig light chain will be generated during the fusion process. These hybrid cells can easily be identified by ELISA assay of the supernatants for the presence of the desired chains and absence of the irrelevant chain.

Thus, in one embodiment, the desired light chain of the final antibody product is the κ light chain. In such cases, a Igλ expressing myeloma cell is transfected with the desired IgH gene. After transfection with a plasmid carrying the desired heavy chain and selection, cells expressing the heavy chain are examined directly for expression of the desired heavy chain, e.g., ELISA assay of the supernatants with antibody specific to the heavy chain. The second cell, e.g., a non-secreting myeloma cell, is transfected with the κ light chain, and transfectants detected through e.g., Northern blot analysis or immuno-detection with an antibody specific to the κ light chain. The cells expressing the light chain can be further selected for desirable characteristics associated with production of a functional light chain, such as light chain production rate or level, ability of the expressed light chain to combine with heavy chain to provide an antibody of a desired antigen binding affinity, and other characteristics desirable for light chain production and heavy chain function in an antibody. The cells are then fused, and the hybrid cell expressing the desired IgH/IgK antibody is selected for the presence of the κ light chain and desired heavy chain (e.g., $C_{65}$) and the absence of λ light chain, e.g., by ELISA assay of the culture medium.

When the desired product antibody contains a λ light chain, the first cell transfected with DNA encoding the desired heavy chain will express a κ light chain, and final selection of hybrid cells expressing the desired antibody will select for the presence of the λ light chain and the absence of the κ light chain.

Figure 4:
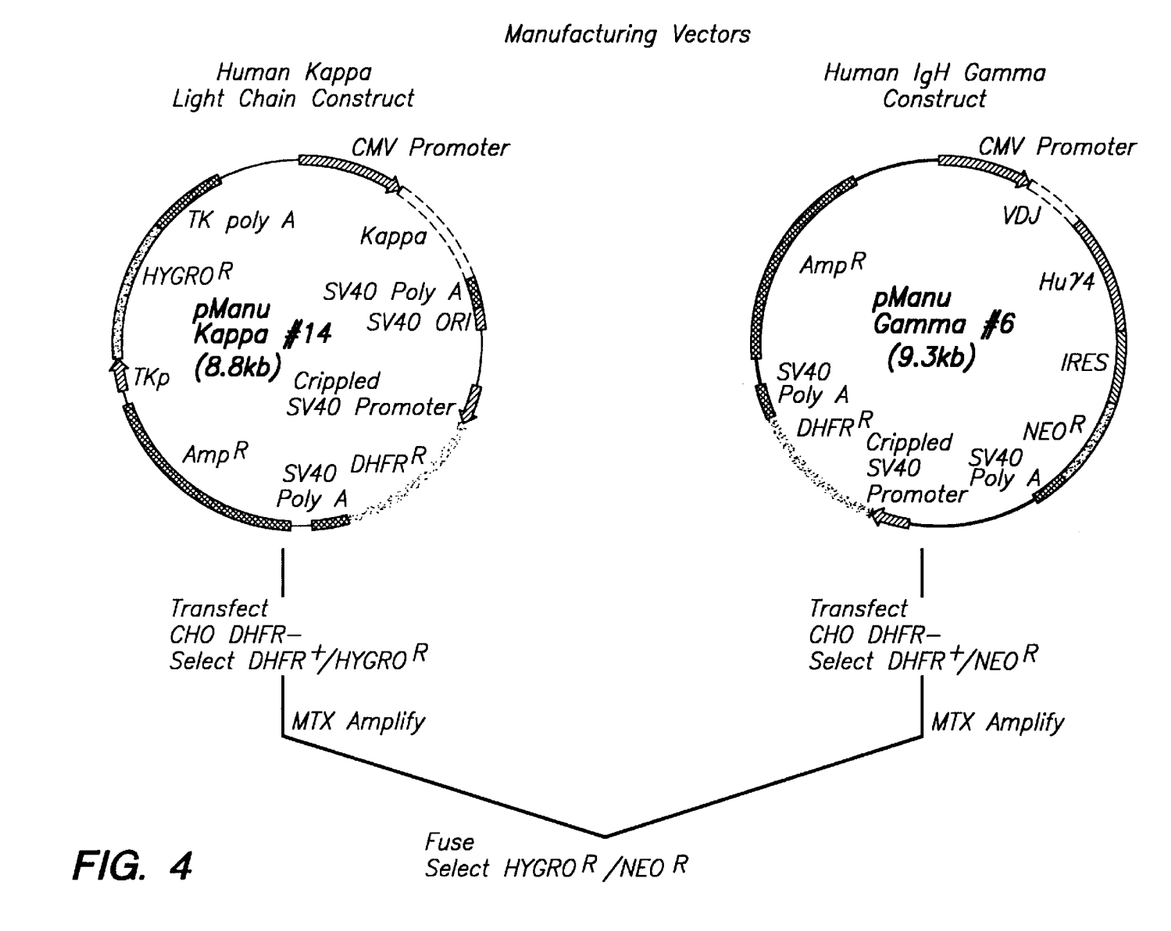
FIG. 4 is a schematic illustrating a specific embodiment of the invention in which DHFR CHO cells are independently transfected with (i) pManuGamma#6, a human heavy chain Ig construct and (ii) pManuKappa#14, a human light chain Ig construct. The independent cell lines are selected, amplified, fused, and selected to yield a hybrid cell containing the human heavy chain Ig construct and the human light chain Ig construct.

In an alternative embodiment of the invention, selection of fused or hybrid cells can be initially determined through the utilization of distinct marker genes in each of the "parental" cells or cell lines. Such technique is shown in FIG. 4. There, a parental CHO cell line, that is DHFR, is transfected with a vector (pManu Kappa) that contains the DHFR resistance gene and the hygromycin resistance gene (HYGRO). Another parental CHO cell line, that is DHFR, is transfected with a vector (pManu Gamma) that contains the DHFR resistance gene and the neomycin resistance gene. Each cell line, following transfection, contains distinct selectable markers (i.e., hygromycin resistance in the first and neomycin/G418 resistance in the second). Thus, upon fusion, resulting "daughter" cells in which fusion has been successful will be resistant to both hygromycin and G418. The screening technique of the invention is advantageous in that it mitigates the need to determine expression of immunoglobulin molecules in order to determine if a fusion has been successfully performed.

Under certain fusion conditions, cells and cell lines can become spontaneously resistant to G418, and, possibly, other selectable markers. Thus, in certain embodiments of the invention, it is preferable to utilize selectable markers to which cells and cell lines are less likely to spontaneously generate resistance. An example of one such marker is the hypoxanthine phosphoribosyl transferase gene (HPRT) which confers resistance to hypoxanthine aminopterin. Another marker that can be used in tandem with HPRT resistance is the LacZ gene. The LacZ gene is not a selectable marker; but, rather, acts as a marker gene which, when expressed by a cell, stains blue in the presence of β-galactosidase.

Thus, through following a similar scheme as described in connection with FIG. 4, a first parental cell line, which is HPRT deficient (such as the P3X, NSO, and NSO-bcl2 myeloma cell lines), is transfected with an antibody gene cassette. The cassette includes, for example, appropriate antibody genes, a gene amplification system, and an HPRT selectable marker. Transfected cells can be selected through HPRT selection and cells producing high levels of antibodies can be picked. A second parental cell line, which is also preferably HPRT deficient, is transfected with an antibody gene cassette. The cassette includes, for example, appropriate antibody genes, a gene amplification system, and the LacZ gene. Transfected cells can be selected through staining with β-gal. As will be appreciated, either the first or second parental cell line can include the light chain genes or the heavy chain genes and the other of the first or second parental cell line will contain the other of the light or heavy chain genes. As will also be appreciated, other selectable markers can be included in the cassettes utilized to transfect the cells. Upon fusion of the first and second parental cell lines, successful fusion can be determined through HPRT selection and β-gal staining of daughter cells. Daughter cells can be further selected based upon expression levels of immunoglobulin molecules.

Figure 5:
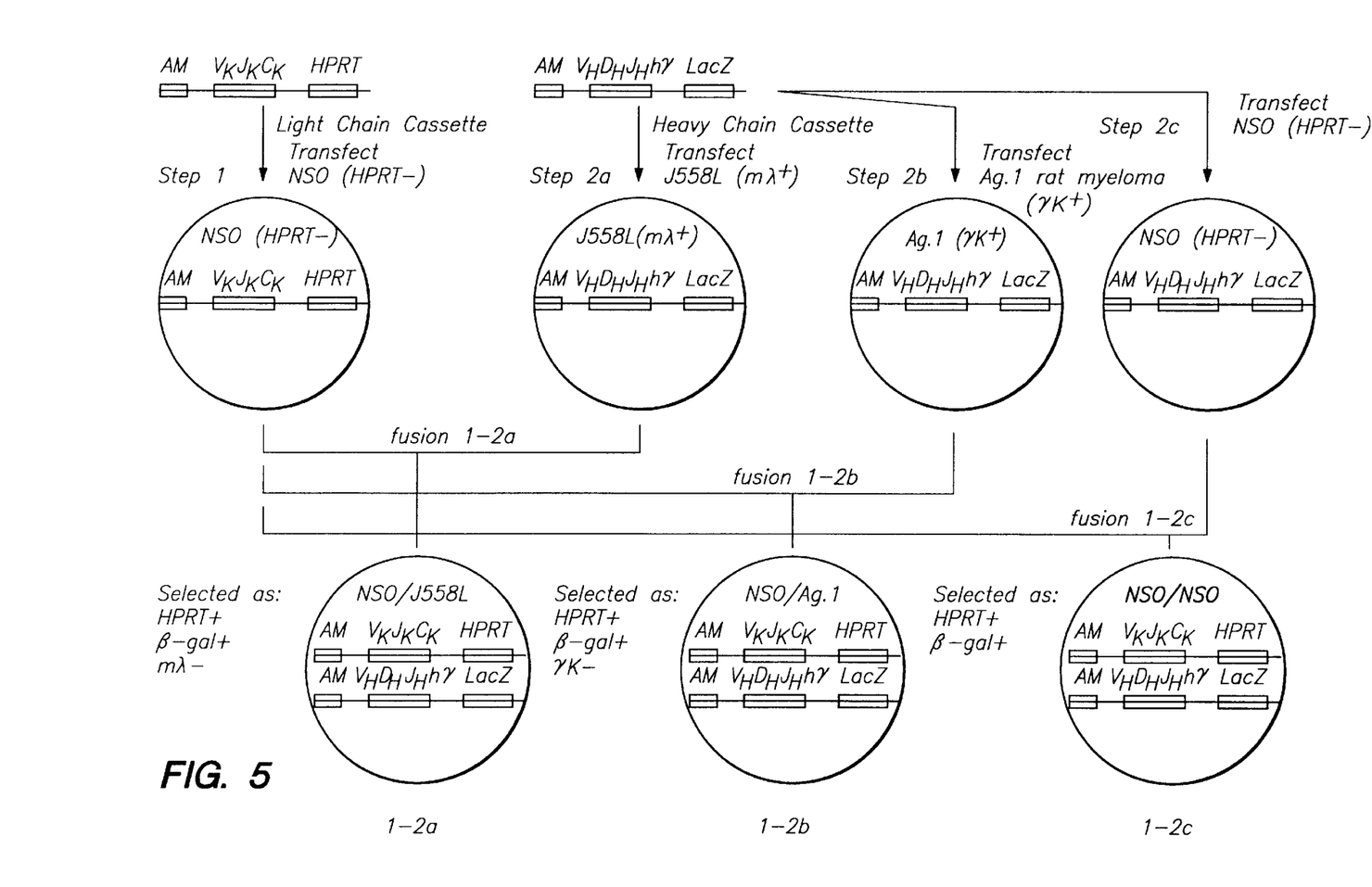
FIG. 5 is a schematic diagram of a fusion method in accordance with the present invention demonstrating the use of HPRT and LacZ marker genes for the initial determination of the success of a fusion process.

Specific embodiments of this technique is illustrated in FIG. 5 in several exemplary schemes. In the Figure, a first parental cell line, exemplified by the myeloma cell line, NSO, which is HPRT deficient, is transfected with a light chain cassette containing a gene amplification system (AM), an antibody light chain gene system ($V_K J_K C_K$), and an HPRT selectable marker (HPRT) (Step 1). A second parental cell line, exemplified by any one of J558L, Ag.1, or NSO, are transfected with a heavy chain cassette containing a gene amplification system (AM), an antibody heavy chain gene system ($V_H D_H J_H h\gamma$), and the LacZ gene (Step 2). The transfection of J558L cell line is indicated as Step 2a, the transfection of the Ag.1 cell line is indicated as Step 2b, and the transfection of the NSO cell line is indicated as Step 2c. With respect of each Step 1 and Steps 2a–2c, the success of the transfection can be determined through the use of the selectable marker HPRT in Step 1 and through β-gal staining in connection with each of Steps 2a–2c. Additionally cells can be picked for expression of light chain (Step 1) or heavy chain (Step 2a–2c).

Following isolation and generation of parental cell lines incorporating the antibody gene cassettes, fusion between a parental cell line including heavy chain genes and a parental cell line including light chain genes is conducted. Utilizing techniques described herein, the parental cell line resulting from Step 1 is fused with a parental cell line resulting from Steps 2a–2c. This is indicated in the Figure as fusion 1-2a, fusion 1-2b, and fusion 1-2c, which results in fused cells 1-2a, 1-2b, and 1-2c, respectively. Such fused cells can be readily identified through dual marker selection, that is, HPRT selection and β-gal staining. Cells which have been successfully fused, will be HPRT resistant and will stain positive with β-gal.

As will be appreciated, the parental cell lines utilized in fusions 1-2a and 1-2b additionally contain mouse mλ and rat λK genes. Thus, daughter cells from fusions 1-2a and 1-2b are preferably selected to ensure that they are mλ and γK. Loss of mouse mλ genes and rat γK genes will generally occur naturally through recombination events during the fusion process.

EXAMPLES

The following examples are put forth so as to provide those of ordinary skill in the art with a complete disclosure and description of how to make and use various constructs and perform the various methods of the present invention and are not intended to limit the scope of what the inventors regard as their invention. Unless indicated otherwise, parts are parts by weight, temperature is in degrees centigrade, and pressure is at or near atmospheric pressure. Efforts have been made to ensure accuracy with respect to numbers used, (e.g., length of DNA sequences, molecular weights, amounts, particular components, etc.) but some deviations should be accounted for.

Example 1
Generation of Hybrid Cells Containing Light and Heavy Ig Chains.

The human heavy chain Ig construct (IgH gamma) was ligated into the pManugamma#6 vector (FIG. 4; Cell Genesys, Inc., Foster City, Calif.) containing DHFR and neo marker genes. The human kappa light chain Ig construct was ligated into the pManukappa#14 (FIG. 4; Cell Genesys, Inc.) which contains DHFR and hygromycin resistance marker genes.

Overview of the Cell Fusion Method

In general, the experiment proceeds as follows: A first cell is transfected with the pManukappa vector comprising the human kappa light chain transgene, and MTX and hygromycin selection marker genes. A second cell is transfected with the pManugamma vector comprising a human $\gamma_4$ heavy chain transgene and Neo and MTX selectable marker genes. After the appropriate selection and amplification, the selected first and second cells are fused to form the hybrid cell of the invention expressing a human antibody.

Cell Transfection

Chinese hamster ovary (CHO) cells are transfected by electroporation as follows: DHFR-deficient CHO cells in exponential growth are fed with growth medium 4 hours prior to electroporation [growth medium: DMEM/Ham's F12 (50:50 mixture; JRH BioSciences, Woodland, Calif.), 10% FBS, 2 mM glutamine, non-essential amino acids (NEAA) plus glycine, hypoxanthine and thymidine (GHT)]. Cells are collected, washed in PBS, and resuspended in PBS to a concentration of $5 \times 10^6$ cells per 0.8 ml. The cell suspension is aliquoted into 0.4 cm electroporation cuvettes (0.8 ml per cuvette) and 5–20 ug linearized DNA added. The suspension is mixed and left on ice for 10 min. Each cuvette is electroporated at 260 V and 960 uF. Each cuvette is place on ice for 10 min, the cells resuspended in 20 ml growth medium, then plated onto 2 10 cm cell culture plates. After 48 hrs, cells from each culture plate are replated in 10 culture plates in the presence of selective media [DMEM, 4.5 g/l glucose (JRH Biosciences), 10% dialyzed FBS (Life Technologies, Bethesda, Md.), 5 mM glutamine, NEAA, 0.6 mg/ml G418].

Selection of Transfectants

Cells transfected with the kappa light chain transgene were selected in the presence of methotrexate (MTX) and hygromycin. Cells were plated 48 hr post-electroporation into 10 plates in DHFR selective media [DMEM, 4.5 g/l glucose (JRH Biosciences), 10% dialyzed FBS (Life Technologies, Bethesda, Md.), 5 mM glutamine, NEAA, supplemented with hygromycin (Calbiochem, San Diego, Calif.) at concentrations ranging from 250–750 ug/ml]. Recombinant protein expression can be increased by DHFR-mediated amplification of the transfected gene. Methods for selecting cell lines bearing gene amplifications are known in the art, e.g., for example, as described in Ausubel et al. (1989) *Current Protocols in Molecular Biology*, John Wiley & Sons, New York; such methods generally involve extended culture in medium containing gradually increasing levels of methotrexate.

Heavy chain transfectant CHO cells are selected in the presence of MTX and neomycin following the above described procedures.

Generation of a Hybrid Cell Expressing an Antibody

Prior to fusion, PEG/DMSO fusion solution (50% PEG, 10% DMSO in PBS)(Sigma) is placed in a 37° C. incubator overnight, and 500–1000 ml incomplete Ham's F12 solution (without FCS) is filtered. At fusion, warm fusion medium and incomplete DMEM/Hams' F12 are placed in a 37° C. water bath. A water-filled beaker and a 15 ml conical tube filled with incomplete DMEM/Ham's F12 are also placed in the water bath. Harvested transfected CHO cells are washed once with incomplete DMEM/Ham's F12, pelleted at 1200 rpm, resuspended in incomplete DMEM/Ham's F12, and counted. The kappa light chain and the $\gamma_4$ transfected cells are mixed in a 1:1 ratio, and centrifuged at 800×g (2060 rpm). The following fusion steps are followed: (1) add 1 ml PEG/DMSO fusion solution to cells over 1 min period; (2) stir cells gently for 1 min; (3) add 2 ml incomplete DMEM/Ham's F12 over a 2 min period with slow stirring; and (4) add 8 ml of incomplete DMEM/Ham's F12 over a 3 min period with slow stirring. The cells are then centrifuged at room temperature at 400×g for 5 min (1460 rpm). Selection medium [complete DMEM/Ham's F12+10% FCS+250–750 ug/ml hygromycin+0.6 mg/ml G418] is added to the cell pellet. 10 ml of selection medium are added to the cell pellet; cells are gently stirred to resuspend.

The cells are plated onto 10 cm dishes as dilutions of 1:10, 1:20, and 1:40 in selection medium. The plates are refed with fresh medium every 3 days until clones appear. Clones are picked and transferred to a 96-well plate in selection medium. As will be appreciated, growth of cells to reach confluence, which demonstrates survival of cells through selection with hygromycin and G418, is indicative that the cells contain both the heavy and light chain Ig genes, since hygromycin resistance was contributed by the light chain gene containing parental cells and neomycin resistance was contributed by the heavy chain gene containing parental cells. As such, dual marker selection provides an expedient method to initially determine whether a fusion has been successfully accomplished. Following such an initial screen, supernatant can be assayed for expression of the desired antibody as described below. When the wells are confluent, the supernatant is assayed for expression of the desired antibody as described below.

Selection for Desired Hybrid Cell

Expression of the desired antibody may be assayed by immunological procedures, such as Western blot or immunoprecipitation analysis of hybrid cell extracts, or by immunofluorescence of intact cells (using, e.g., the methods described in Ausubel et al. (1989) supra). The desired antibody is detected using antibody specific for each component of the desired antibody, e.g., antibodies specific to the kappa light chain and $\gamma_4$ heavy chain.

Confirmation of Desired Characteristics of Antibody Produced by Hybrid Cell

After the hybrid cell is produced and antibody production in the cell is confirmed, the hybrid cell is grown under conditions to allow expression of the antibody and secretion of the antibody into the cell culture supernatant. For example, the cells can be grown in roller bottles in selective growth medium (DMEM/Ham's F12 (50:50 mixture), 10% FBS, 2 mM glutamine, non-essential amino acids plus glycine, hypoxanthine and thymidine, plus hygromycin and G418 to provide continued selection for the heavy and light chain constructs in the hybrid cell) for several hours prior to assay. Cell culture supernatant is collected and the antibodies are tested for various desired characteristics, e.g., antigen binding affinity (e.g., preferably antigen binding affinity that is similar to that of the original antibody from which the recombinant antibody is derived) using immunological assays well known in the art (e.g., ELISA, or competition binding assays).

The instant invention is shown and described herein in what is considered to be the most practical and the preferred embodiments. It is recognized, however, that departures may be made therefrom which are within the scope of the invention, and that obvious modifications will occur to one skilled in the art upon reading this disclosure.

What is claimed is:

1. A method for producing an antibody, said method comprising:
    (a) introducing an expression vector comprising a nucleotide sequence encoding a heavy chain into a first mammalian host cell;
    (b) introducing an expression vector comprising a nucleotide sequence encoding a light chain into a second mammalian host cell; and
    (c) fusing the first and second cells to form a hybrid cell, wherein the hybrid cell expresses an antibody comprised of the heavy chain and the light chain.

2. The method of claim 1, further comprising:
    (d) culturing the hybrid cells so as to express the antibody; and
    (e) recovering the antibody from the hybrid cell culture.

3. The method of claim 1, wherein the nucleotide sequence encoding a heavy chain and the nucleotide sequence encoding a light chain are each obtained from a B-cell or a hybridoma cell, wherein said B-cell or hybridoma cell produce an antibody.

4. The method of claim 1, wherein the first cell expresses both an irrelevant light chain and the heavy chain prior to fusion with the second cell.

5. The method of claim 1, wherein expression of the heavy chain by the first cell is determined by ELISA analysis of lysate from the first cell.

6. The method of claim 1, wherein the antibody is expressed only after fusion of said first and second mammalian cells.

7. The method of claim 1, wherein the first cell expressing the heavy chain is further selected for based on its rate of antibody production.

8. The method of claim 1, wherein both the second cell expressing the light chain and the first cell expressing the heavy chain are each further selected for based on their rate of production.

9. A method for producing an antibody, comprising:

(a) introducing an expression vector comprising a nucleotide sequence encoding a heavy chain into a first mammalian host cell, wherein the first cell expresses an irrelevant light chain;

(b) introducing an expression vector comprising a nucleotide sequence encoding a light chain into a second mammalian host cell; and (c) fusing the first and second cells to form a hybrid cell, wherein the hybrid cell expresses an antibody comprised of the heavy chain encoded by the introduced nucleotide sequence and the light chain encoded by the sequence introduced in the second cell.

10. The method of claim 9, further comprising:

(d) culturing the hybrid cells so as to express the antibody; and (e) recovering the antibody from the hybrid cell culture.

11. The method of claim 9, wherein the irrelevant light chain in the first cell is present in an episomal vector.

* * * * *